United States Patent [19]

Mir

[11] Patent Number: 5,468,223

[45] Date of Patent: Nov. 21, 1995

[54] ELECTROCHEMOTHERAPY

[75] Inventor: Lluis Mir, Verrières le Buisson, France

[73] Assignee: C.N.R.S. Paris, Villejuif Cedex, France

[21] Appl. No.: 983,172

[22] Filed: Nov. 30, 1992

[51] Int. Cl.$^6$ .................................................. A61M 31/00
[52] U.S. Cl. .................................. 604/51; 604/20; 604/52
[58] Field of Search .................................. 604/76, 49, 51,
604/52; 128/898

[56] References Cited

U.S. PATENT DOCUMENTS

| | | | |
|---|---|---|---|
| 4,558,690 | 12/1985 | Joyce | 604/20 |
| 4,622,952 | 11/1986 | Gordon | 604/20 |
| 4,955,378 | 9/1990 | Grasso | 604/20 |
| 5,019,034 | 5/1991 | Weaver et al. | 604/20 |
| 5,286,254 | 2/1994 | Shopland et al. | 604/21 |
| 5,304,120 | 4/1994 | Crandell | 604/21 |
| 5,389,069 | 4/1995 | Weaver | 604/21 |

OTHER PUBLICATIONS

"Signals and Systems" Alan V. Oppenheim, 1983 Prentice–Hall p. 193.
Abdul Hamied et al., *Cancer Immunol Immunother* 25:245–249 (1987).
Auerbach et al., *Cancer Res.* 38:1739–1744 (1978).
Bazile et al., *Biochem Biophys. Res. Commun.* 159:633–639 (1989).
Belehradek et al., *Eur. J. Cancer* 27:73–76 (1991).
Briefings—"Shock Therapy Helps Kill Cancer Tumors" *Science* 255:539 (31 Jan. 1992).
Crooke et al., *J. Med.* 7:333–428 (1976).
Heller et al., *Analytical Biochemistry* 202:001–007 (1992).
Heller et al., *Biochimica et Biophysica Acta* 1024:185–188 (1990).
Hirsch et al., *J. Immunol.* 140:3766–3772 (1988).
Kanesada, K., *J. Jpn. Soc. Cancer Ther.* 25:2640–2648 (1990).
Leo et al., *Proc. Natl. Acad. Sci. USA* 84:1374–1378 (1987).
Mir et al., *C.R. Acad. Sci. Paris*, t. 313, Serie III 613–618 (1991).
Mir et al., *C.R. Acad. Sci. Paris*, t. 314, Serie III 539–544 (1992).
Mir et al., *Eur. Cytokine Netw.* 3:331–334 (1992).
Mir et al., *Eur. J. Cancer* 27:68–72 (1991).
Mir et al., *Exp. Cell Res.* 175:15–25 (1988).
Morikawa et al., *Cancer Res.* 45:1502–1506 (1985).
Morikawa et al., *Cancer Res.* 46:684–688 (1986).
Okino et al., *Jpn. J. Cancer Res.* 78:1319–1321 (1987).
Okino et al., *Jpn. J. Cancer Res* 83:1095–1101 (1992).
Okino et al., *Jpn. J. Surgery* 20(2):197–204 (1990).
Okino et al., *Proc. Jpn. Cancer Congress* 46:420 (1987).
Orlowski et al., *Biochem Pharmacol* 37:4727–4733 (1988).
Poddevin et al., *Biochem Pharmacol* 42 (Suppl.):S67–S75 (1991).
Roy et al., *Cancer Res.* 44:1541–1546 (1984).
Titomirov et al., *Biochimica et Biophysica Acta* 1088:131–134 (1991).
Xu et al., *Cancer Res.* 48:6658–6663 (1988).

*Primary Examiner*—C. Fred Rosenbaum
*Assistant Examiner*—Mark Bockelman
*Attorney, Agent, or Firm*—Fish & Richardson

[57] ABSTRACT

This invention provides for methods of introducing anticancer agents directly into cancer cells by increasing the permeability of cell walls through the use of electric pulses.

9 Claims, 6 Drawing Sheets

ELECTROCHEMOTHERAPY

BACKGROUND OF THE INVENTION

This invention relates generally to the use of electric impulses to increase the permeability of cancer cell walls, and, more specifically to providing access of anticancer drugs directly into the cancer cell cytosol.

The effectiveness of many anticancer drugs is limited by the inability of the drug to penetrate the cancer cell membrane. Although the dosage of the drug may be increased in order for the drug to have its desired effect on the target cell, such increases in dosages often result in the death of host cells. The need exists, therefore, for a method of introducing cancer drugs into the target cancer cell while at the same time minimizing the death of healthy host cells.

The present invention solves this problem through a technique known as "electrochemotherapy." Electrochemotherapy, involves the application of electric pulses to a target cell resulting in the increased permeability of the cell membrane. This increased permeability by electric pulses, known as "electroporation," allows a greater number of the anticancer drug molecules to enter the target cell's membrane. This further allows a much lower concentration of the drug to be introduced without sacrificing efficacy and at the same time reducing or eliminating conventional side effects.

The use of electrical impulses on the biological membrane has been generally known. Techniques such as electroporation and electrofusion have been utilized in many areas of the biomedical sciences. Electrofusion is a process by which membrane fusion can be induced by exposure to electrical fields. Electrofusion has many practical applications such as the formation of hybridomas, the production of monoclonal antibodies, the study of membrane fusion mechanisms, and the examination of cytosolic events. In addition, electrofusion has proved to be a valuable tool in examining membrane interaction between two cells or within a single cell. Materials can also be introduced into cells by utilizing liposomes encapsulated with the selected material and then fusing with the recipient cells. Additionally, individual cells can be incorporated into intact tissue in a process known as cell-tissue electrofusion.

Electroporation techniques have also been used in a variety of situations for a variety of purposes. For example, electroporation has been used to transfect genetic material into target cells (Titomirov et al., *Biochimica et Biophysica Acta*, 1088:131–134 (1991)). In addition, studies of the effects of high-voltage electrical impulses with an anticancer drug on an in vivo growing malignant tumor has been studied (Okino, *Jpn. J. Cancer Res.*, 78:1319–1321 (1987)). However, this technique required the penetration of the host organism's skin tissue in order to directly apply the electrical impulses. Furthermore, previous techniques have resulted in widespread destruction of host cells thus neutralizing any added benefit of the lower dosage rates of the anticancer drug (See discussion, Weaver et al., U.S. Pat. No. 5,019,034)). Only one attempt to combine bleomycin and electric pulses in vivo has been reported (Okino et al., *Jpn. J. Cancer Res.* 78:1319–1321 (1987)). Mohri and Okino obtained partial regression (PR) of AH-109A hepatocellular carcinoma in Donryu rats after the combined administration of bleomycin and one exponentially decaying intense (5000 V/cm, 2 ms) pulse. However, these conditions produced oedema even in the absence of drug and caused necrosis of the surrounding skin when used in combination with bleomycin.

SUMMARY OF THE INVENTION

The present invention provides a method of treating tumors in vivo by increasing the permeability of the tumor cells through local use of electrical impulses. This invention further involves electrochemotherapy, the use of electric impulses in combination with one or more anticancer drugs to enhance the effectiveness of anti-tumor treatment. This invention also involves a method of treating tumors where electrochemotherapy is followed by the introduction of cytokines or lymphokines or genes which produce these substances as expression products.

mice receiving only 2 daily IP injections of 5000 IU of IL-2; o: mice receiving 10 μg bleomycin and 2 daily injections of IL-2; Δ: mice receiving the electric pulse and 2 daily injections of IL-2.

Figure 11:
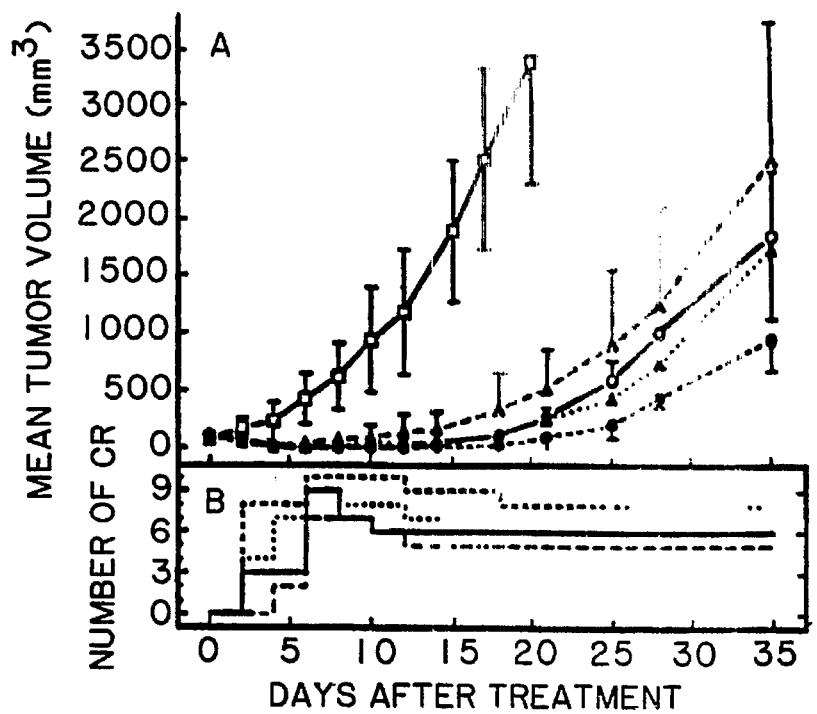

FIG. 11 shows electrochemotherapy followed by treatment with interleukin-2 administered intraperitoneally. Panel A: Mean tumor volume of the mice which were not in complete regression (CR) after the electrochemotherapy. Panel B: Number of CR amongst 10 treated mice. —□—: control untreated mice; —o—: electrochemotherapy using 10 μg bleomycin; ——●——: electrochemotherapy using 10 μg bleomycin and then 2 daily injections of 5000 IU IL-2. . . . Δ . . . : electrochemotherapy using 2 μg bleomycin; . . . ▲ . . . : electrochemotherapy using 2 μg bleomycin and then 2 daily IP injections of 5000 IU of IL-2.

Figure 12:
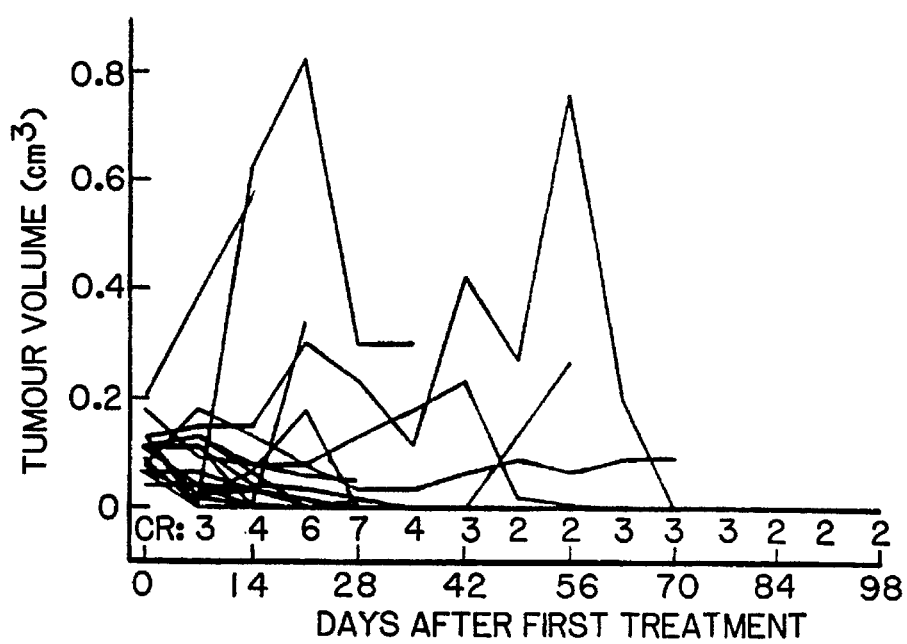

FIG. 12 shows the effect of electrochemotherapy on small spontaneous mammary tumors of C3H/Bi mice.

Figure 13:
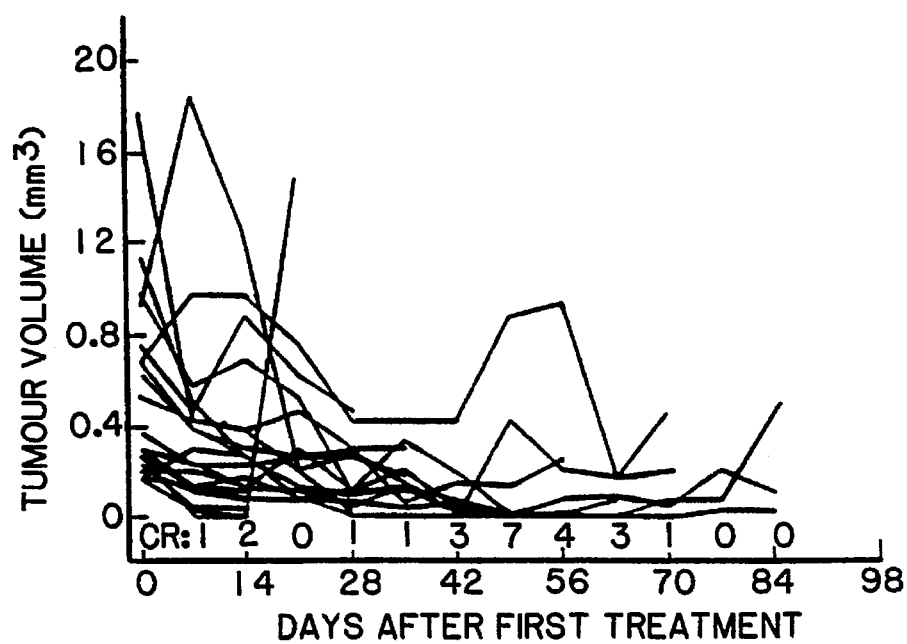

FIG. 13 shows the effect of electrochemotherapy on large spontaneous mammary tumors of C3H/Bi mice.

Figure 14:
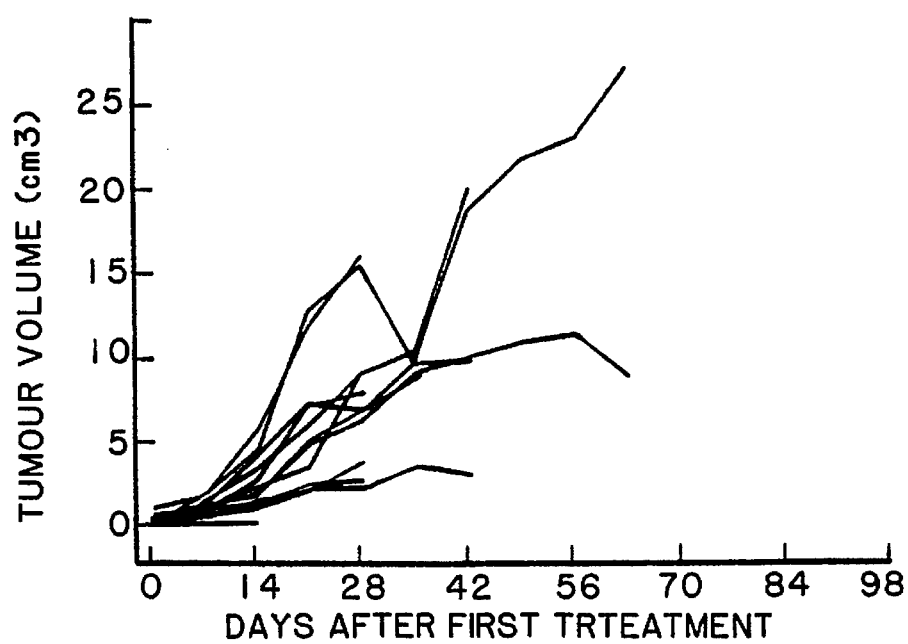

FIG. 14 indicates the growth curves of control tumors.

DETAILED DESCRIPTION OF THE INVENTION

The present invention provides a method of treating in vivo tumor cells through a technique known as "electrochemotherapy." This method involves the application of electrical impulses to the affected organism. The application of these impulses, results in increased permeability of the tumor cells. This increased permeability results in higher concentrations of the drug in the target tumor cells' cytoplasm, thus vastly increasing the drug's effectiveness against the target cell. This invention also provides a method whereby actual penetration of the organism's tissues is not required except as may be necessary for the injection of the anticancer drug(s). This invention also provides a method whereby a combination of anticancer drugs may be introduced into the target cells cytoplasm. Moreover, this invention provides a method of effectively treating tumors whereby an anticancer drug is systemically introduced. Also provided is a method of introducing an immunomodulator such as a cytokine or lymphokine to further enhance the antitumor effect of the anticancer drug.

A comparison was made of the in vitro cytotoxicity of a panel of anticancer drugs on intact cells and on cells submitted to short, intense, square-wave electric pulses (Orlowski et al., *Biochem Pharmacol*, 37:4727–4733 (1988)). Bleomycin, is a cytotoxic agent currently used in some anticancer combinations. The drug causes DNA single and double strand breaks by a catalytic mechanism. However, the diffusion of bleomycin through the plasma membrane is slow and only limited amounts enter the cells. Roy et al., *Cancer Res.*, 44:1541–1546 (1984).

After electric pulse delivery, a substantial reduction (about 700 times) was observed in bleomycin concentration, which reduces cloning efficiency to 50% of controls ($EC_{50}$). Moreover, after electric field treatment, bleomycin was cytotoxic even at very low external concentrations (starting from $10^{-9}$ mol/l) with a steep dose-response curve. The relative gain in toxicity depends on the survival level considered: it has been observed that the external bleomycin concentration required to kill 90% of treated cells (i.e., $EC_{10}$) was reduced 650,000 times after electric field treatment conditions that do not affect cell viability in the absence of the drug (Orlowski et al., supra).

Applying the method of the present invention in conventional C57B1/6 mice, at least partial regressions were observed in 100% of the murine LPB and B16 syngeneic tumors, and under the most efficient conditions up to 50% cures. Human KB tumors in nude mice also regressed considerably after electrochemotherapy. As suggested by previous in vitro data, the increased permeability of the tumor cells after electric field application should, at least partly, account for the potentiation observed in vivo.

In more appropriate conditions as in the present work, electrochemotherapy is appealing because of the extent to which bleomycin's antitumor activity was potentiated. Preliminary experiments with bleomycin doses as low as 0.5 μg achieved deceleration of tumor growth similar to that observed with the non-potentiated high doses of bleomycin (1 mg per day for 5 days). Thus, the in vivo potentiation obtained by the electric treatment was about 10,000 fold.

These results suggest that a substantial fraction of the tumor cells was killed by the combined treatment. However, all the cells were not probably killed. Indeed, a great difference in response to the same treatment of the same LPB tumor between immunodeficient nude mice and immunologically reactive C57B1/6 mice was observed. Thus, the host's immune response could be instrumental in the elimination of tumor cells after massive cell lysis due to electrochemotherapy.

Whatever the mechanism of potentiation, the local presence of the electric field is essential. First, a minimum intensity of the electric field of at least 1100–1200 V/cm was required for drug potentiation. Secondly, it was repeatedly observed that all tumor areas that were not exactly between the electrodes escaped treatment and continued to grow with a slope identical to that of control animals which received bleomycin alone. These findings suggest that most of the treatment failures in C57B1/6 mice can be explained by the fact that the corresponding tumors slightly exceeded the maximum area covered by the electrodes.

The toxicity observed during the experiments on C57B1/6 mice can be partly explained by the dose of bleoymcin (500 μg, i.e., one-tenth of the $LD_{50}$) and by the fact that, due to the slenderness of the mice, the so-called treatment was in fact a regional treatment. Indeed, necropsy revealed that the external portion of the liver (just beneath the tumor) was also necrosed when treated tumors were located at the right flank. This observation probably explains the difference in toxicity observed during the treatment of tumors located either at the right or at the left flanks. Nevertheless, this toxicity is not a problem since, in bigger animals or in man, local treatment will have a genuine local action without secondary regional effects and a lower dose (50 μg instead of 500 μg) proved to be efficient and did not cause death (Example V, Table 3).

Thus, in vivo, the local potentiation of bleomycin by electric pulses results in substantial antitumor activity even with the administration of small amounts of drug which limits side-effects. Electric pulses could also be used with other poorly permeable molecules, such as oligonucleotides directed against oncogene expression products. These molecules have specific targets and can discriminate between transformed and normal cells; however, oligonucleotides do not enter intact cells easily. Nevertheless, their uptake is increased in vitro after exposure of cells to electric fields (Bazile et al., *Biochem Biophys. Res. Commun.*, 159:633–639 (1989)).

It was previously reported that, with the same transplanted murine tumor, electrochemotherapy resulted either in 30% of cures in the syngeneic immunocompetent mice or in the absence of any cure in the immunodeficient nude (nu/nu) mice, (Mir et al., *Eur J. Cancer*, 27:68–72 (1991)). Histology of treated nodules revealed massive cell lysis in both situations. This effect of the bleomycin plus electric pulse can be related to the results obtained using cells in suspension, in which electropermeabilization increases bleomycin uptake and, consequently, bleomycin cytotoxicity (Orlowski et al., supra; Poddevin et al., *Biochem Pharmacol*, 42(S):67–75 (1991)). Nevertheless, in vitro, the permeabilization, nor the killing, of 100% of the cells submitted to electric pulse was never achieved (Leo et al., *Proc. Natl. Acad. Sci. USA*, 84:1374–1378 (1987); Hirsch et al., *J. Immunol.*, 140:3766–3772 (1988); Mir et al., *Exp. Cell Res.*, 175:15–25 (1988)). Thus, in vivo, the combined treatment using bleomycin plus electric pulse would have been expected to lead to an incomplete killing of the tumor cells. Nevertheless, cures, i.e., complete eradication of the tumor cells, was really achieved. It was postulated that the host's immune system is involved in the destruction of the residual cells surviving to the direct lytic effects of electrochemotherapy.

The $OKT_3$ MoAb is known to induce a considerable transient immunosuppression by causing a rapid and complete depletion of all the mature T-lymphocytes at the level of the peripheral organs (Hirsch et al., *J. Immunol*, 140:3766–3772 (1988)). After electrochemotherapy, fewer cures were achieved in $OKT_3$ treated mice than in controls and the oedema was absent or very reduced. In contrast, IL-2 injections alone were ineffective but higher cure rates were achieved when IL-2 was administered (at a dose much lower than conventionally used) after electrochemotherapy. This demonstrates that the cure achievement implies the contribution of the T-cell mediated host's immune response.

Figure 7:
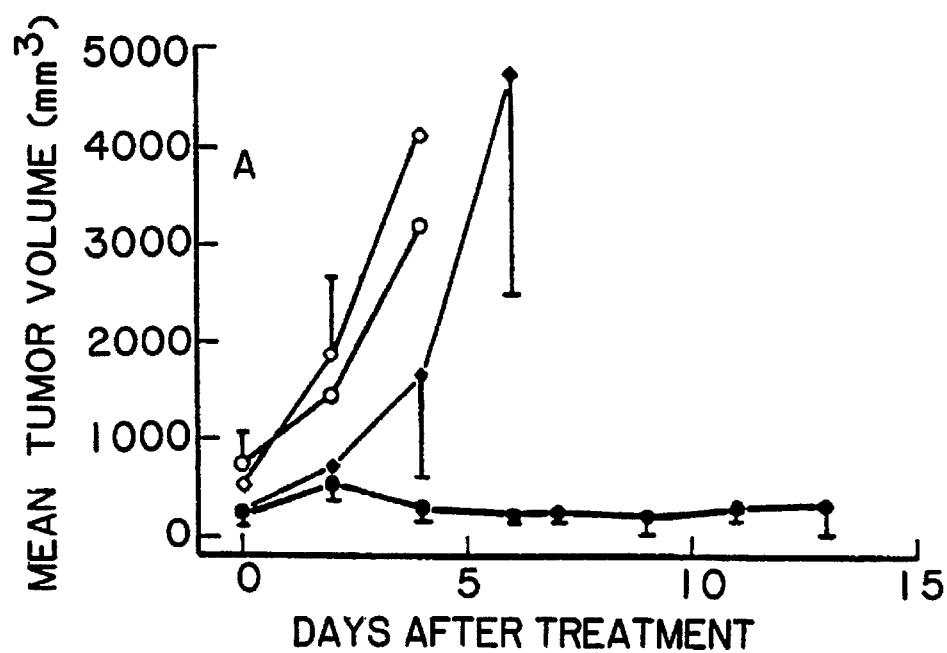
FIG. 7 shows the effects of bleomycin and electric pulses on B16 melanomas in flanks of C57B1/6 mice. Mean tumor volumes until day 13. ●=D+E+, o=D+E−, ♦= D−E+ and ◊=D−E− mice.
Figure 8:
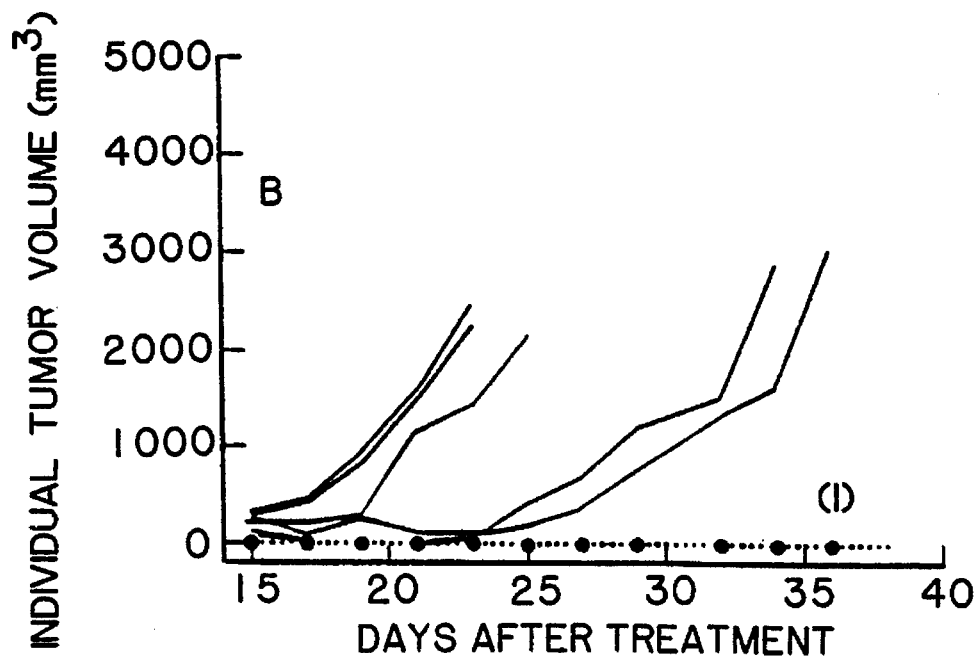
FIG. 8 shows the individual course of D+E+ tumors from day 15 onwards (8 survivors out of 11 treated mice). At day 17, 3 mice had CR (●). 1 late recurrence (at day 23) is shown in right part of figure.

The four control groups reported in FIG. 7 are indistinguishable from each other. This suggests that, in the conditions presented here, no immunomodulatory effects of bleomycin can be evoked. However, it has been reported that in vivo bleomycin can either enhance IL-2 release (Abdul Hamied et al., *Cancer Immunol Immunother*, 25:245–249 (1987)), or modulate cell immunity by eliminating suppressor T-cells (Morikawa et al., *Cancer Res.*, 45:1502–1506 (1985); Xu et al., *Cancer Res.*, 48:6658–6663 (1988)), or by increasing the tumoricidal activity of the macrophages (Morikawa et al., *Cancer Res.*, 46:684–688 (1986)). In fact, these immunomodulatory effects have been observed with doses at least 10 fold greater than those used in the present study, and in therapeutical protocols involving repeated administration of bleomycin for 5 days.

In one embodiment, three therapeutic elements are used: a drug that was previously thought to be only effective at high doses inducing secondary effects, a physical treatment which can cause cell death at high dose and an immunomodulator which is not well tolerated at therapeutical doses. Surprisingly, the association of low doses of each element, all of them inefficient per se and devoid of side effects, leads to the achievement of a high rate of cures.

The above described drug is not limited to bleomycin, but includes any drug which has an antitumor effect or cytotoxic effect. Drugs contemplated also include non-permeant or semi-permeant molecules. The invention also encompasses molecules which become active inside the cell and/or whose target is intracellular. This includes the introduction of oligonucleotides including but not limited to those which are directed against the oncogene RNA. The above described immunomodulator includes cytokines and lymphokines. A cytokine is any soluble molecule which mediates interactions between cells. A lymphokine is a molecule other than an antibody produced by lymphocytes and which is involved in signaling between cells of the immune system. These include interleukins, interferons, tumor necrosis factor, and colony stimulating factors.

The drug may be administered through systemic or local injection or may be introduced directly to the tumor site. The drug may also be topically applied.

The immunomodulator may be introduced either locally or systemically. It may be further introduced by introduction of the immunomodulator gene into the tumor cells or by introduction of allogenic cells capable of producing the immunomodulator.

This invention also involves a method of providing systemic immunity whereby electrochemotherapy is followed by direct injection of cytokines of lymphokines or genes which produce these substances as expression products.

The following specific examples are provided to enable those skilled in the art to practice the invention. The examples should not be considered limitations upon the scope of the invention, but merely as being illustrative and representative thereof.

EXAMPLE I

Preparation of cells utilized in murine in vivo tests

The highly tumorigenic murine LPB cell line is a clonal derivative of TBL.C12, a methylcholanthrene-induced C57B1/6 mouse sarcoma cell line (Belehradek et al., *Int. J. Cancer*, 9:461–469 (1972)). The B16 melanoma cells, syngeneic to C57B1/6 mice, were obtained by trypsin dissociation of tumors serially passaged in vivo. KB cells were derived from cultures of a recently explanted tumor previously initiated in a nu/nu mouse with the KB human oral epidermoid carcinoma cell line (Eagle, *Proc. Soc. Exp. Biol. Med.*, 89:362–364 (1955)). These cells are utilized in Examples II and III.

EXAMPLE II

In vivo treatment of cell inocula

Either 50,000 or 5000 LPB cells (suspended in 100 µl culture medium) were subcutaneously injected into the four legs of pentobarbital anaesthetized (40 mg/kg) 6–8 week old nu/nu mice with Swiss background (from Institut Gustave Roussy). This unusual inoculation site was chosen because it facilitates the placement of the two flat rectangular electrodes on each side of the cell inoculum. Contact between the electrodes and the skin was ensured by means of electrocardiography paste. Sex and age matched animals were randomly assigned to four experimental groups, each consisting of six mice (i.e., 24 legs inoculated). No statistically significant differences in tumor growth on the anterior and the posterior legs were observed.

Bleomycin (Laboratories Roger Bellon) was added to the cell suspension just before the injection: cells were injected in the absence (D–) or in the presence (D+) of 0.5 µmol/l bleomycin (which corresponds to a dose of 75 ng locally injected into animals weighing about 25 g). Electric treatments, consisting of 8 pulses of 100 µs and 1500 V/cm at 1 Hz were (E+) or were not (E–) administered at the inoculum site immediately after cell inoculation. To assess the tumor latency period, was scored the day on which a nodule of 3 mm in diameter appeared.

Results

A bleomycin concentration was chosen that in vitro was unable to kill more than 10% of cells not exposed to electric fields but which was at least 5 fold the concentration necessary to kill in vitro 100% of LPB cells thus exposed. No macroscopic signs of necrosis were observed on the skin under the electrodes. Locomotion was not impeded in the treated animals. The only secondary effect observed was a potentiation of the pentobarbital-induced anaesthesia.

Figure 1:
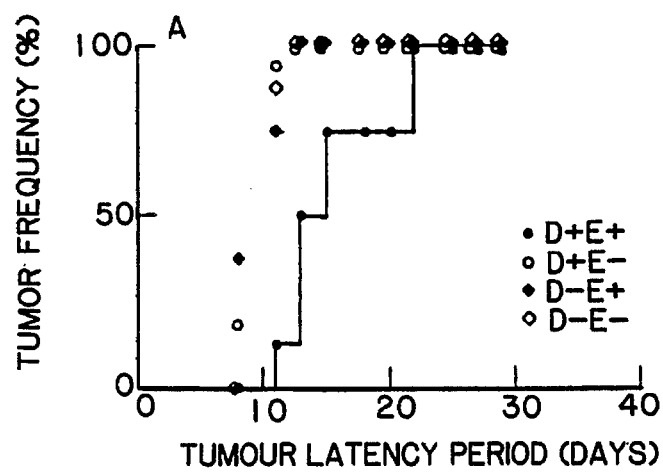
FIG. 1 shows the increase of latency period before tumor appearance after electrochemotherapy on inocula of 50,000 cells in legs of nude mice.
Figure 2:
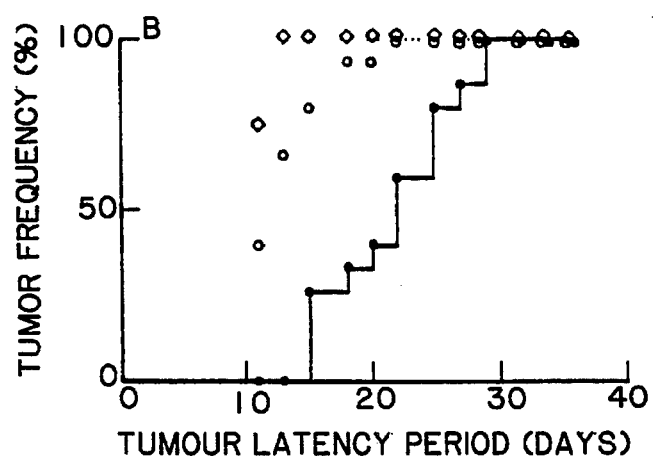
FIG. 2 shows the increase of latency period before tumor appearance after electrochemotherapy on inocula of 5000 LPB cells in legs of nude mice.

Three independent experiments were done with inocula of 50,000 LPB cells in the legs of nude mice and yielded similar results. One typical experiment is shown in FIG. 1: the median number of days before the appearance of tumors was 14.3 for the mice which received both cells suspended in bleomycin and electric pulse delivery (D+E+) and 10.5 (D−E−), 10.3 (D−E+) or 10.5 (D+E−) for the control groups. The tumor latency periods for the three control groups were not mutually significantly different (Duncan and Tukey tests on harmonic means), whereas the delay in tumor growth in the D+E+ group was significant ($P<0.01$). Since the number of LPB injected cells (50,000) was above the minimal cell number necessary to initiate a tumor, additional experiments were done with as few as 5000 LPB cells per inoculum. The effect of bleomycin combined with electrical pulses on the delay in tumor growth was greater (FIG. 2): the median number of days before the appearance of tumors was 21.7 for the D+E+ group compared with 10.6 (D−E−) and 12.6 (D+E−). The delay in tumor growth observed in the D+E+ group compared with that of the control groups was again significant ($P<0.01$). These data suggest that only a small fraction of cells survived electrochemotherapy. Thus, in vivo, electrical pulses delivered via the skin potentiated bleomycin's cytotoxicity to fresh inocula of suspended cells.

EXAMPLE

Tumor treatment in mice

To produce solid tumors, either 150,000 LPB cells or $2\times10^6$ KB cells were injected subcutaneously into flanks of nude mice, and either 150,000 LPB cells or $10^6$ B16 cells into the flanks of C57B1/6 mice. The tumors of about 7 mm in average diameter (the maximum size which could be encompassed by the electrodes utilized with a distance of 6.6 mm between them and 10 mm long) were obtained 7–9 days later. Animals bearing tumors were then randomized into four experimental groups designated D+E+, D+E−, D−E+ and D−E−, each comprising usually 10 mice (n=6 for experiments in KB cells).

The animals of the D+E+ and D+E− groups received two intramuscular injections of 250 µg bleomycin into both thighs (i.e., total dose 500 µg, which corresponds to roughly one-tenth of the $LD_{50}$ (Crooke et al., *J. Med.*, 7:333–428 (1976)). 30 min after bleomycin injection, the amount of time necessary to allow bleomycin to reach the tumor (Crooke et al., Supra), the D+E+ animals received electric pulses (1500 V/cm, 100 µs, 1 Hz, 8 pulses) delivered with electrodes placed on both sides of the protruding tumor. Contact was ensured by electrocardiography paste. The D−E+ group received the same electric pulses without a bleomycin injection. The D−E− group received neither bleomycin nor electric pulses.

The tumor's longest diameter (a) and the next longest diameter (b) perpendicular to a were measured with a caliper at regular times. The tumor volume was calculated by $V=ab^2\pi/6$, derived from the formula previously developed by Auerbach et al., *Cancer Res.*, 38:1739–1744 (1978). The mean (S.D.) tumor volume were calculated.

Objective responses were scored as: (i) partial regression (PR), (ii) complete regression (CR) and (iii) cure according to World Health Organization guidelines. The therapeutic result was termed cure if CR at a particular site was maintained without recurrence at least 120 days after treatment.

Results

Figure 3:
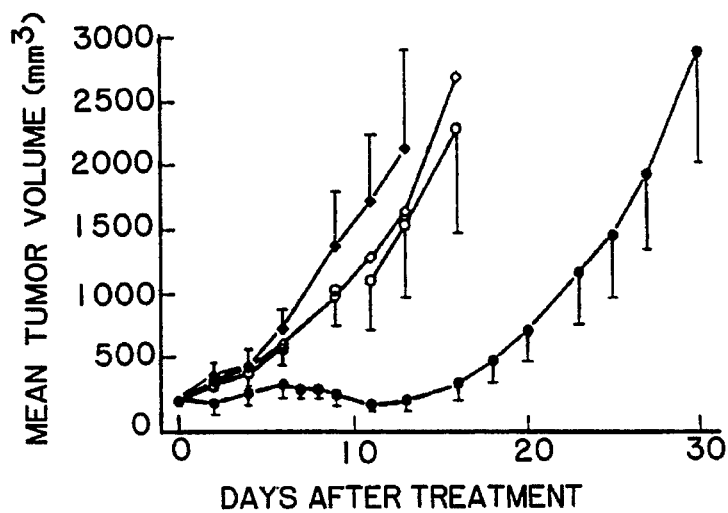
FIG. 3 shows the effects of bleomycin and electric pulses on LPB sarcomas in flanks of nude mice. ●= D+E+; o D+E−; ♦=D−E+ and ◊=D−E−; where D=bleomycin, E=electric treatment, and ± indicates the presence or absence of D or E.

An arrest of LPB tumor growth was observed in all mice receiving electrochemotherapy (n=14), whereas bleomycin alone (n=10 animals) or electric pulses alone (n=10) had no effect on tumor growth compared with the control D−E− group (n=10 animals) (FIG. 3). The regression of tumor volume in the D+E+ mice was partly masked by local oedema: the consistency of the volumes measured was more flaccid than that of the untreated tumors. Transient skin scabs were observed under the electrodes after electrochemotherapy. They progressively disappeared within 2–3 weeks. However, necrosis of the tumor tissue was found on histological sections as early as 24 h after treatment. Nevertheless, in nude mice, LPB tumors were never completely eradicated: after a transient interruption in growth (and a probable PR masked by oedema) of 12–15 days, tumor progression resumed with growth slopes similar to those of control tumors.

Figure 4:
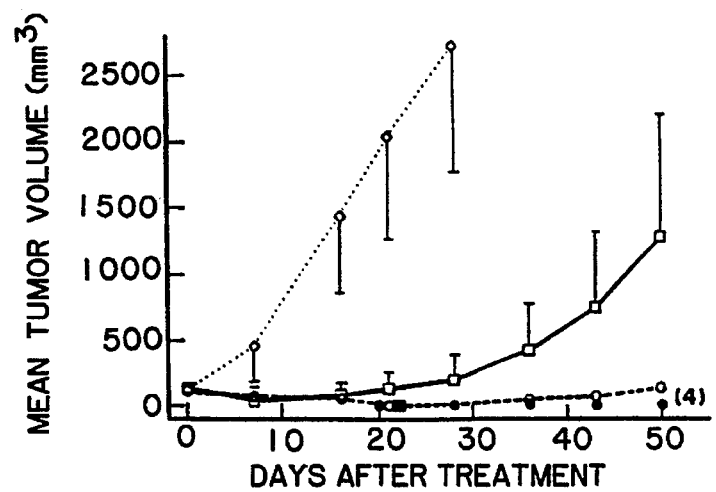
FIG. 4 shows the effects of bleomycin and electric pulses on KB carcinomas in flanks of nude mice. o=500 and □=50 µg bleomycin. For controls only the D+E− group has been drawn (◊). S.D. not drawn in right part of dashed curve as only 1 mouse showed recurrence. ■=1 transient CR, mouse treated with 50 µg bleomycin (this value was not included in calculation of mean tumor volume); ●=CRs, D+E+ mice treated with 500 µg bleomycin. No. in brackets refers to 4 CRs still at day 50 among 6 treated mice.

For the KB carcinomas treated under the same conditions, CRs were observed in all the D+E+ treated mice; only 1 early recurrence was detected later (FIG. 4). For animals with longer CR, tumors did not reappear 50 days after the treatment. KB carcinomas were also treated with only 50 µg bleomycin and the same electrical field. Tumor growth was arrested in all cases and 1 transient CR was detected at day 22 (FIG. 4).

EXAMPLE IV

Tumor treatment in C57B1/6 mice

Figure 5:
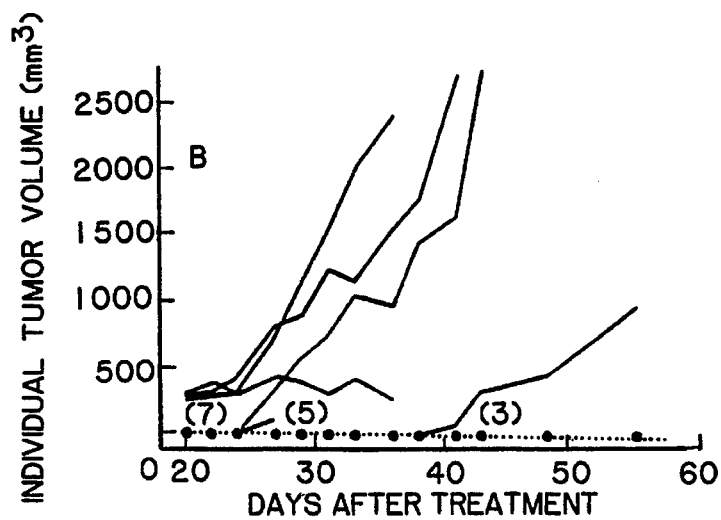
FIG. 5 illustrates the effects of bleomycin and electric pulses on LPB sarcomas in flanks of C57B1/6 mice. Mean tumor volumes until day 17. D−E+ group was omitted in this experiment; when it was done, it never differed significantly from the other two controls, namely D+E− and D−E− (see also FIGS. 3, 7 and 8). ●=D+E+, o=D+E− and ◊=D−E− mice. Lines show individual recurrences. No. in brackets refers to CRs achieved.
Figure 6:
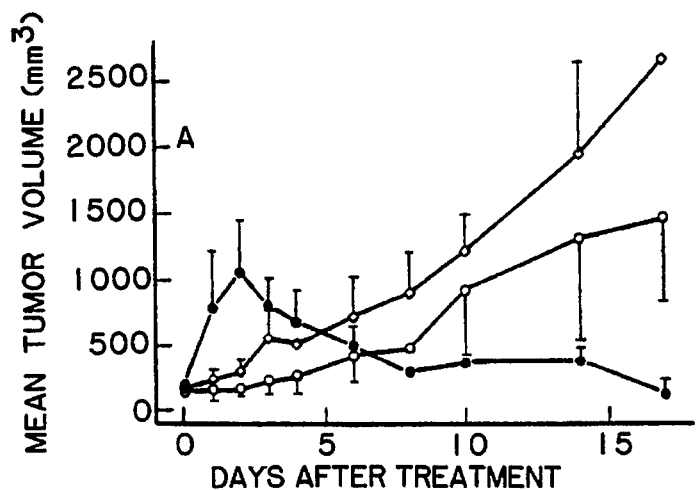
FIG. 6 illustrates the individual course of D+E+ tumors from day 20 onwards (10 survivors out of 16 treated mice) 7 mice had CR (●). Lines show individual recurrences. No. in brackets refers to CRs achieved.

In immunologically reactive C57B1/6 mice bearing LPB sarcomas, a more severe oedema than that found in nude mice was always detected at the tumor site after electrochemotherapy with 500 µg bleomycin. This resulted in a rapid increase in the mass perceivable, which, nevertheless, began to regress 3–4 days later (FIG. 5). Oedema was never detected in controls. In mice with LPB tumor in the right flank (FIG. 5), after combined treatment, 6 out of 16 D+E+ mice died after 4–10 days without, however, any further development of tumor. Necropsy and histological examination revealed necrosis in the external part of the liver, just beneath the treated tumor. 20 days after electrochemotherapy, sarcomas disappeared completely in 7 of the remaining 10 mice (FIG. 6). Of these 7, 2 developed an early recurrence (at day 23) and 1 a late recurrence at day 41 (FIG. 6); 1 animal was killed at day 45 for necropsy and histological examination which confirmed the absence of tumor tissue; 1 animal died without any apparent tumor; and 2 mice were cured (absence of tumor 250 days after the treatment).

Similar results were obtained in C57B1/6 mice bearing LPB tumors at the left flank, except that only 3 of 21 animals died a few days after treatment, again without any further tumor development. Among the 18 survivors, 4 CRs were observed. Two were still free of their initial tumor 210 days after the combined treatment.

These experiments were extended by applying the same combined treatment to C57B1/6 mice bearing transplantable syngeneic B16 melanoma in their left flank. The growth of this tumor was extremely rapid for the three control groups whereas an excellent response to electrochemotherapy was obtained (FIG. 7). After a transient increase in volume at the tumor site, oedemas and tumors regressed. Overall, 4 mice had CR. 17 days after the treatment, tumor was no longer detectable in 3 out of 8 surviving animals (the D+E+ group initially contained 11 mice). In 1 case, tumor had not reappeared 200 days later.

An additional control experiment was done to compare these results with the most active treatment with bleomycin alone—a daily intramuscular injection of 1 mg for 5 consecutive days in C57B1/6 mice bearing LPB sarcoma. This dose is not far from the lethal dose and had a considerable toxic effect: weight ss, hirsutism and death a few days later. A deceleration was noted, however, in tumor growth rate, which was more likely related to general bleomycin toxicity than to a specific antitumor effect. No tumor growth arrest was observed.

EXAMPLE V

Variations of electrochemotherapy modalities

Table 1 shows the biological and therapeutic efficiency of the combined treatment according to the electric field intensity applied. From 1500 V/cm (initial conditions) down to 1200 V/cm, electric fields remained as effective on LPB tumors (at the left flank), both after short and long intervals following combined treatment. Most of the animals which achieved CR at day 27 were cured. Overall, 35% of the treated mice (18 out of 51) were cured after a combined treatment, whatever the electric field used between 1500 and 1200 V/cm. At lower voltages, fewer CRs were observed, more recurrences occurred (1 as late as day 65 and another on day 98) and fewer (1100 V/cm) or no cures (below 1100 V/cm) were obtained. Thus, with 500 µg bleomycin and 8 pulses, the minimal efficient field intensity required was 1100–1200 V/cm.

TABLE 1

EFFECTS OF SINGLE COMBINED TREATMENT OF LPB SARCOMAS AS FUNCTION OF INTENSITY OF ELECTRIC PULSES (500 37 µg BLEOMYCIN)

| V/cm | Day 0 | Day 11 | Day 27 | Day 120 |
|---|---|---|---|---|
| 1500 | | | | |
| Mean (S.D.) | 69(39) | 76(33) | 810(550) | |
| Tumors | 12 | 3 | 7 | 0 |
| CR | — | 8(66%) | 4(33%) | 3(25%) |
| 1400 | | | | |
| Mean (S.D.) | 72(52) | 23(14) | 520(360) | |
| Tumors | 13 | 2 | 8 | 0 |
| CR | — | 11(85%) | 4(31%) | 4(31%) |
| 1300 | | | | |
| Mean (S.D.) | 55(31) | 47(41) | 1100(700) | |
| Tumors | 13 | 6 | 4 | 0 |
| CR | — | 7(54%) | 8(61%) | 7(54%) |
| 1200 | | | | |
| Mean (S.D.) | 50(24) | 20(19) | 820(900) | |
| Tumors | 13 | 3 | 7 | 0 |
| CR | — | 9(69%) | 4(31%) | 4(31%) |
| 1100 | | | | |
| Mean (S.D.) | 46(24) | 68(32) | 1100(1500) | |
| Tumors | 13 | 3 | 10 | 0 |
| CR | — | 10(77%) | 3(23%) | 3(23%) |
| 1000 | | | | |
| Mean (S.D.) | 43(14) | 33(53) | 1700(1800) | |
| Tumors | 7 | 4 | 6 | 0 |
| CR | — | 3(43%) | 1(14%) | 0 |
| 900 | | | | |
| Mean (S.D.) | 70(42) | 85(59) | 1500(1200) | |
| Tumors | 6 | 4 | 5 | 0 |
| CR | — | 2(33%) | 1(17%) | 0 |
| 0 | | | | |
| Mean (S.D.) | 32(32) | 430(300) | 4300(2400) | |
| Tumors | 8 | 8 | 8 | 0 |
| CR | — | 0 | 0 | 0 |

Less easy to quantify was the constant observation about local cutaneous and subcutaneous reactions. The more the electric field was reduced, the more oedema and scabs were attenuated or disappeared rapidly. Similarly, no death was observed after the combined treatment when 1400 V/cm or less intense electric fields were applied (in Table 1, only 1 early death was observed, at 1500 V/cm).

Short-term experiments on C57B1/6 mice bearing a LPB tumor in the left flank revealed that, both at 1500 and at 1200 V/cm, combined treatment with 3 pulses instead of 8 also indiced substantial regressions (Table 2). Local reactions, however, were different. After 3 pulses at 1200 V/cm, oedema was almost absent and 3 days after the treatment, already 5 CRs were observed among 30 treated tumors. At 1500 V/cm and 3 pulses and at 1200 V/cm and 8 pulses, oedema was still found but regressed more rapidly than after 8 pulses delivered at 1500 V/cm. Consequently, CR, unmasked by local inflammatory reaction, could be detected earlier. Moreover, no deaths were observed when only 3 pulses were delivered, even at 1500 V/cm. Long-term follow-up showed no major differences in the number of pulses used in the combined treatment (Table 2).

TABLE 2

EFFECTS OF ELECTROCHEMOTHERAPY ON LPB SARCOMAS AS FUNCTION OF NUMBER OF PULSES AND OF PULSE INTENSITY (500 µg BLEOMYCIN)

| | 1500 V/cm | | | 1200 V/cm | | |
|---|---|---|---|---|---|---|
| | Day 0 | Day 7 | Day 120 | Day 0 | Day 7 | Day 120 |
| 8 pulses | | | | | | |
| Tumors | 33 | 7 | 0 | 21 | 6 | 0 |
| CR | — | 24(73%) | 5(15%) | — | 12(57%) | 6(29%) |
| 3 pulses | | | | | | |
| Tumors | 20 | 0 | | 30 | 13 | 0 |
| CR | — | 20 (100%) | 3*(30%) | — | 17(57%) | 2†(20%) |

Early deaths occurred with 8 pulses (2 and 3 mice treated with 1500 and 1200 V/cm, respectively).
*Only one cage of 10 mice out of two and †only one cage out of three were followed up to day 120.

C57B1/6 mice bearing LPB tumor in the left flank received three weekly combined treatments at 1500 V/cm with only 3 pulses and only 50 µg bleomycin per treatment to reduce the cutaneous and subcutaneous reactions as well as the global drug toxicity (Table 3). A single treatment at this reduced dose of bleomycin was as efficient as a single treatment with ten times more (compare Tables 1 and 3). When treatment with the low dose was repeated three times, efficacy was enhanced (Table 3). Indeed, the repeated combined treatments resulted in 50% cures and no signs of cumulative drug toxicity.

TABLE 3

EFFECTS OF SINGLE OR THREE-TIMES REPEATED ELECTROCHEMOTHERAPY (1500 V/cm) ON LPB SARCOMAS WITH 50 µm BLEOMYCIN

| | Day | | | | |
|---|---|---|---|---|---|
| | 0 | 7 | 20 | 35 | 120 |
| Once | | | | | |
| Mean (S.D.) | 84(42) | 4 | 180(200) | 1900(1100) | |
| Tumors | 10 | 1 | 6 | 7 | 0 |
| CR | — | 9(90%) | 3(30%) | 3(30%) | 3(30%) |
| Thrice | | | | | |
| Mean (S.D.) | 56(50) | | | 420(580) | |
| Tumors | 10 | 0 | 0 | 4 | 0 |
| CR | — | 10(100%) | 10(100%) | 6(60%) | 5(50%) |

EXAMPLE VI

Materials and methods used in MoAb/IL-2 studies

Bleomycin (Laboratory R. Bellon, Neuilly, France) was dissolved in sterile 0.9% NaCl. The monoclonal antibody (MoAb) $OKT_3$ (Leo et al., *Proc. Natl. Acad. Sci. USA*, 84:1374–1378 (1987); Hirsch et al., *J. Immunol*, 140:3766–3772 (1988)), was a kind gift from Dr. L. Chatenoud (INSERM U25, Paris, France). Recombinant IL-2 (240 µg/ml; $20\times10^6$ international units (IU)/mg) was provided by Dr. P. Ferrara (Sanofi-EBR, Labége, France).

Obtention of indifferentiated chemoinduced mouse sarcoma LPB tumors of 6 to 7 mm of average diameter, as well as tumor evolution and tumor volumes were determined as previously described (Mir et al., *Eur. J. Cancer*, 27:68–72 (1991); Belehradek et al., *Eur. J. Cancer*, 27:73–76 (1991)). The average diameter of the peritumoral oedema which appears at the tumor site after electrochemotherapy was also observed. Electrochemotherapy was performed as previously described except that 100 µl of bleomycin solution were injected IV in the retroorbitary sinus 3 to 3.5 minutes before electric pulse delivery. Square wave electric pulse (1500 V/cm, 100 µs, 1 Hz, 8 pulses) were generated by a PS 15 electropulsator (Jouan, France).

EXAMPLE VII

Electrochemotherapy of mice treated with $OKT_3$ monoclonal antibody

Figure 9:
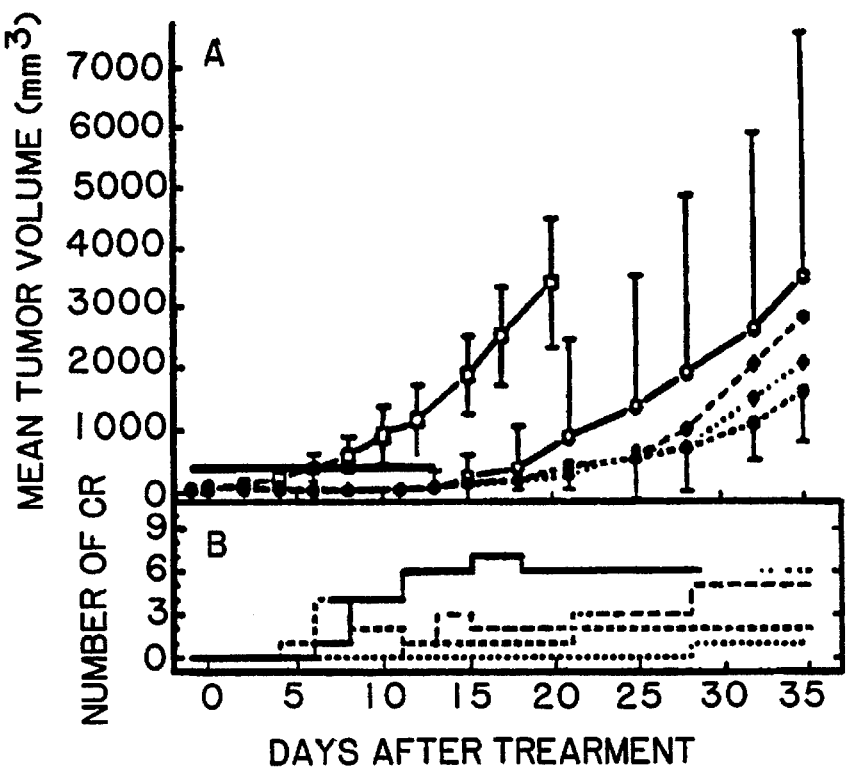
FIG. 9 shows electrochemotherapy of mice treated with $OKT_3$ monoclonal antibody. Panel A: Mean tumor volume of the mice which were not in complete regression (CR) after the electrochemotherapy. Panel B: Number of CR amongst 10 treated mice. —□—: control untreated mice; —o—: electrochemotherapy using 10 µg bleomycin; ... ● ... : electrochemotherapy, using 10 µg bleomycin, of $OKT_3$ MoAb treated mice; ... ◊ ... electrochemotherapy, using 50 µg bleomycin; ... ♦ ... of $OKT_3$ MoAb treated mice.
Figure 10:
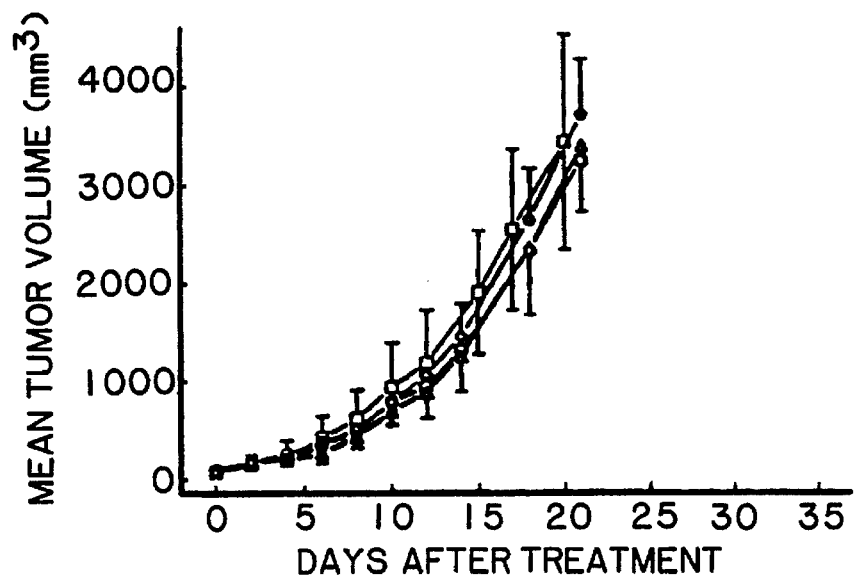
FIG. 10 shows tumor evolution in mice receiving an incomplete electrochemotherapy. □: untreated mice; ◊.

The day before electrochemotherapy, one group of randomized tumor bearing mice received one IV injection of 5 µg of the $OKT_3$ MoAb. Two other injections were performed 24 and 72 hours after electrochemotherapy. At the time of electrochemotherapy, all the $OKT_3$ treated mice exhibited poor general status accompanied by a considerable (15%) loss of weight. There was also a pause in tumor growth, mean tumor volume (MTV) reaching $88\pm27$ mm$^3$ after $OKT_3$ and $129\pm48$ mm$^3$ in the non injected mice. The therapeutic effect of electrochemotherapy using 10 µg of IV bleomycin in the group of the $OKT_3$ treated mice was worse than that observed in the control group of mice treated with electrochemotherapy-only (FIG. 9). A peritumoral oedema was present only in 4 out of 10 $OKT_3$ treated mice. In addition, only 2/10 $OKT_3$ treated mice were cured in this experimental group. This contrasts with the usual rate of cures (6/10) obtained in the 10 mice control group (FIG. 9B).

An additional experiment was performed using 50 µg of IV bleomycin per mouse. In controls, i.e., electrochemotherapy without $OKT_3$ MoAb, a very pronounced peritumoral oedema was observed (mean diameter: $15.2\pm0.8$ mm a day 1 vs $10.3\pm1.1$ mm with 10 µg of IV bleomycin) and 4/10 animals were cured (FIG. 9B). $OKT_3$ again provoked a reduction in MTV at the time of electrochemotherapy: $61\pm28$ MM$^3$ instead of $101\pm71$ mm$^3$. The mean diameter of peritumoral oedema after $OKT_3$ and electrochemotherapy was reduced ($9.2\pm1.2$ mm at day 1) compared to control mice and only 1 cure was obtained.

EXAMPLE VIII

Electrochemotherapy and immune response reinforcement by IL-2 injection

Electrochemotherapy (i.e., 10 µg bleomycin plus EP) treated mice showed results identical to those independently obtained with the same bleomycin dose during the $OKT_3$ assays (FIGS. 9 and 11). When IL-2 was administered after electrochemotherapy (i.e., bleomycin plus electric pulse plus IL-2, in this order), no significant changes in the size of the peritumoral oedema was observed. All mice (10 out of 10) exhibited complete regression. Only 2 recurrences were observed (FIG. 11B), later than in mice treated by electrochemotherapy alone. As one animal died without tumor before the sixtieth day (i.e., the time limited used for the definition of a cure), only 7 mice were scored as definitively cured.

Electrochemotherapy was also performed with a lower dose of bleomycin (2 µg) followed by the IP IL-2 treatment: 9 mice out of 10 exhibited complete regression and 6 mice were cured (FIG. 11B). In this case, electrochemotherapy alone was slightly less efficient than electrochemotherapy using 10 µg of bleomycin (5 cures, FIG. 11B).

EXAMPLE IX

Effect of electrochemotherapy on spontaneous mammary tumors of C3H/Bi mice

Materials—A colony of C3H/Bi mice, naturally infected by the Bittner murine mammary tumor virus (Staats, *Cancer Res.*, 45:945–977 (1986)), is maintained at the Institut Gustave-Roussy. Females are mated two to three times as soon as they are adult. Mammary tumors appear in these multiparous mice at 5–11 months of age. In most of the animals additional tumors appear at different sites and at various times after their initial tumor(s). Untreated animals die within 1–2 months after the detection of their first tumor(s).

Electrochemotherapy—Electrochemotherapy was repeated every week until 1 week after the nodule was no longer palpable. Briefly, bleomycin (Laboratoires R. Bellon) was injected intramuscularly in the thighs of 10 mice (50 µg in 50 µl saline) 30 min before the delivery of square-wave pulses with a commercially available generator (Bioblock) (Orlowski, supra). The distance between the electrodes (two stainless steel strips, 10 mm in width) was 6.7 mm. Six randomly assigned mice received bleomycin alone as controls. In the study of several other tumor models [2], the electric pulses in the absence of bleomycin were not cytotoxic in vitro (Orlowski, supra).

In "small" tumors, only one run of electric pulses was delivered. A run of electric pulses consisted of 8 pulses of 100 μs and of 1500 V/cm at 1 Hz. In "large" tumors, several runs (2–5) of electric pulses were applied at adjacent positions to cover the entire exposed tumor surface.

Assessment of response—The tumor's longest diameter (a) and the next longest diameter (b) perpendicular to a were measured with a caliper at regular times. The mean diameter of individual tumors was calculated at 0.5 (a+b). Tumor volume was calculated by $V = ab^2 \pi/6$, derived from the formula developed by Auerbach et al., (*Cancer Res.*, 38:1739–1744 (1978)).

Since the mice frequently develop more than one tumor, each tumor was scored individually. The course of the individual tumors after electrochemotherapy was scored as: (i) partial regression (PR); (ii) complete regression (CR); and (iii) cure. According to World Health Organization guidelines, the therapeutic result was termed PR if the initial tumor volume decreased by at least 50% and CR if the tumor became palpable. The result was termed cure if the CR achieved at a given tumor site was maintained with recurrence until the animal's death at least 60 days after the first treatment of that tumor.

Because the stock of old multiparous C3H/Bi females were searched for new tumors weekly, tumors had often reached a size that could not be entirely encompassed by the electrodes. Before this series of experiments, as a rule, electrochemotherapy was applied to tumors of less than 6.7 mm in mean diameter, which corresponded roughly to the maximum distance between the two electrodes. Tumors included in the present study were classified according to their mean diameter on the day of first treatment: small if less than or equal to 6.7 mm, and large if greater than 6.7 mm.

Results

Small tumors—Almost all the tumors regressed, at least partially, within 2–3 weeks (Table 4, FIG. 12). As early as 7 days after the first treatment, 6 tumors showed PR and 3 CR. Among the 9 remaining tumors, 7 achieved PR or CR later, 1 decreased to 80% of initial volume and only 1 continued to grow. Among the 10 CRs, only 3 recurred. For the remaining 7 CRs, follow-up was not long enough to score the CR as a cure because the animals died within 60 days after the first treatment of the tumor concerned.

TABLE 4

EFFECT OF ELECTROCHEMOTHERAPY

| Size | No. of tumors | PR | CR | Cures |
|---|---|---|---|---|
| Small | 18 | 3 (17%) | 10 (56%) | 3 (17%) |
| Large | 20 | 10 (50%) | 10 (50%) | 0 |

In fact, follow-up was often limited in time because most of the mice developed new tumors at various sites during the treatment of their initial tumor(s). For this reason electrochemotherapy was not interrupted when the initial tumor was in CR because these animals were treated continuously at other tumor site(s). Thus, after 10–12 successive treatments, the weekly administration of bleomycin sometimes led to death from cumulative toxicity. Thus, since long-term follow-up of most of the CRs was not possible, the number of cures is probably an underestimation. Despite the fact that follow-up for more than 60 days was only possible for 5 of the 18 treated small tumors, as many as 3 cures were achieved.

An unusual course in one of the treated small tumors is worth mentioning. After three treatments, this tumor showed a growth arrest only and after the fourth treatment, electrochemotherapy was stopped. The size of the tumor remained constant for 2 further weeks and only after decreased. CR was observed 6 weeks after treatment stopped and no additional tumors appeared during this period. Thus, after the four treatments, although regression was not immediately evident, the tumor tissues seemed to be efficiently inactivated.

Large tumors—Most of the large tumors rapidly achieved PR or CR (Table 4, FIG. 13). Obviously, the complete disappearance of palpable nodules was later than that for small tumors. Again, the evaluation of cures was not easy since the progressive appearance of new tumors in the animals under treatment and the constraint of a continuous weekly treatment leading sometimes to cumulative bleomycin toxicity did not allow a substantial gain in survival. Among the 10 CRs, 1 was in an animal which died without signs of recurrence at day 58 (i.e. 2 days before limit for classification as a cure). Three other tumors were in CR at day 60 but they were not considered as cures because recurrence or new equivocal tumors located close to the initial tumor sites appeared at day 77 (FIG. 13).

Some large tumors showed a distinct course. They stopped growing but showed only limited regression. After 5–6 weeks of treatment, a scab was visible at the tumor site. Below the scab, the consistency of the tumor mass was not firm. During manipulation of these mice, the scab broke and a semi-solid necrotic substance was spontaneously extruded. By gently pressing the site, it was possible to remove the necrotic tumor mass almost completely. Thus, even if no reduction was observed in tumor size, necrosis supervened.

Furthermore, in two of these large tumors, growth persisted under the scab and necrotic mass. After 2–3 weeks, this led to a column-shaped nodule consisting of clearly necrotic tissue except at the base. It is thought that the scab and the necrotic tissue had formed a structure limiting the access of the electric field to the part of the tumor where growth persisted. Thus, removal of part of the necrotic mass might allow deeper penetration of the field.

Control tumors—Neither PR nor even growth arrests were observed in control mice (FIG. 14). Only a slight reduction in tumor growth rate was detected after six to seven bleomycin injections, which was probably related to the large tumor size reached at that time and not directly to drug activity. Moreover, it was sometimes difficult to measure tumor size (e.g., if tumors on the same animal became confluent). Given the limited number of tumor bearing animals available for study, a control group treated by electric pulses without bleomycin was not included.

Survival—There was an overall increase in survival of treated mice from the day of the detection and the first treatment of their initial tumor(s) compared with controls (Table 5). The median survival of the treated mice (82 days) was nearly double that of the controls (47 days). However, this increase was not significant (P= 0.06, Wilcoxon rank-sum test).

The reliable detection of new additional tumors in control animals was only feasible within the first month after the detection of the first tumor of each mouse, when initial tumors were not yet too large. During this period, 8 new tumors were detected in the 6 control mice and 8 in the 10 treated mice (Table 5). This situation contrasts with the data on the overall appearance of additional tumors (22 in treated and 8 in controls). The increased survival of the treated mice may explain the fact that more additional tumors were detected in treated mice than in controls. At the time of detection of the first tumor, the median age in both groups of mice was similar. When mice were examined individually, no correlation was noted between tumor occurrence and age.

TABLE 5

AGE, SURVIVAL AND TIME OF APPEARANCE OF ADDITIONAL TUMORS

|  | Age (mo) | Survival (days) | Appearance of additional tumors (days) |
|---|---|---|---|
| Treated |  |  |  |
| 1 | 10 | 123 | 21 28 63 |
| 2† | 9 | 39 | 14 |
| 3† | 10 | 121 | 49 55 63 |
| 4† | 9 | 65 | 14 41 41 49 |
| 5† | 7 | 82 | 7 28 |
| 6 | 11 | 29 | — |
| 7 | 11 | 48 | 24 |
| 8 | 5 | 219 | 120 157 |
| 9 | 8 | 108 | 61 70 70 89 |
| 10† | 8 | 73 | 7 49 |
| Median | 9.2 | 82 |  |
| Control |  |  |  |
| 1 | 8 | 67 | — |
| 2 | 9 | 42 | — |
| 3 | 9 | 29 | 21 |
| 4 | 6 | 68 | — |
| 5 | 8 | 47 | 4 7 14 26 |
| 6 | 9 | 45 | 14 16 16 |
| Median | 8.7 | 47 |  |

EXAMPLE X

Tumor treatment in humans

Patients—Seven patients with permeation nodules (cutaneous metastases) of head and neck squamous cell carcinomas were treated at the Institute Gustave-Roussy. No patient had received bleomycin before the electrochemotherapy. All the treated nodules were located in the anterior cervical region or in the upper part of the thorax. They were measured and photographed before and after treatment. As a precaution, patients remained hospitalized for 24 hours. Then they were examined 5 days after and later when possible.

Treatment conditions—Electrochemotherapy consists in the intravenous administration of bleomycin followed by the delivery of transcutaneous electric pulse through external electrodes located on each side of the nodule. Sedatives (Table 6) were administered 1 hour before the start of electrochemotherapy. The intravenous injection of bleomycin, at the dose of 10 mg/m$^2$ irrespective of the number of nodules treated, was followed by 3,5 minutes later by electric pulse to the 1st nodule. Electric treatment consisted of a run of 4 or 8 (Table 6) square waved electric pulse of 100 μs and 1,300 V cm$^{-1}$, delivered at the frequency of 1 Hz by a PS 15 electropulsator (Jouan, France). When more than 1 nodule was treated during the same session, electric pulse runs were delivered one after another, at intervals of at least 1 minute. Electrodes were 2 stainless steel strips 10 mm large, 0.6 mm thick and 6 mm apart. Contact with skin was ensured by means of electrocardiography paste.

Results

Twenty-eight nodules were treated with a single run of 4 or 8 electric pulse per nodule, and 6 larger nodules with several runs delivered at adjacent positions to cover, as much as possible, the entire exposed tumor surface (Table 6). During these treatments, no significant alteration of pulse rate or blood pressure was noticed. Instantaneous contractions affecting muscles of the neck and the shoulders were observed, which disappeared immediately after each electric pulse. Patients characterized the contractions as painless. However, they described a short unpleasant sensation, not related to the contractions, that vanished as soon as electric pulse stopped.

One to 2 hours after the treatment, the only visible effect was the occurrence of erythema and of a slight oedema, just at the site of the treated areas, both disappearing in less than 24 hours. In some cases, signs of leuconecrosis of the nodules were visible the day after. Patients reported neither local delayed pain nor any other clinical sign. Marks of the electrodes were visible after 2 sessions, FAR 2 and ROM. (See Table 6, column 1 identifies individual electrochemotherapy sessions).

In all cases the growth of the treated nodules was at least slowed down as compared with that of the neighboring nodules, not submitted to the electric pulse but exposed to the same bleomycin dose. Furthermore, in the 1st patient, all of the 11 small nodules which were correctly flanked by the electrodes disappeared as well as 1 large nodule reaching 20 mm in diameter (Table 6). Two other sessions (MIC 1 and ROM) resulted again in the complete disappearance of the treated nodules.

This phase I study is the first clinical trial of a new antitumor treatment, electrochemotherapy. It reveals that electrochemotherapy is quite feasible since it does not cause unbearable side effects. No serious incident, either general or local, occurred in spite of the bad health status of most of the patients. Furthermore, in vitro studies on the cellular pharmacology of bleomycin as well as preclinical trials on mice suggest that electrochemotherapy may be applied to tumors of different histological origin: hence, these results show both electrochemotherapy feasibility in man and a clear antitumor efficiency are encouraging for further electrochemotherapy developments.

TABLE 6

|  |  |  |  |  | EXAMPLE X |  |  |  |
|---|---|---|---|---|---|---|---|---|
|  | Premedication/ Induction | Nod | BLM (mg) | n | PL | Contr. | Secondary Effects | Therapeutic Effects |
| FAR 1 | Lorazepan 2,5 mg PO | 1 | 17 | 4 | + | + | Slight local | 1 RCL/48 Days |
| FAR 2 | Lorazepam 2,5 mg | 11 | 17 | 4 | +++ | ++ | Slight local | 1 RCL/34 Days |

TABLE 6-continued

EXAMPLE X

|  | Premedication/ Induction | Nod | BLM (mg) | n | PL | Contr. | Secondary Effects | Therapeutic Effects |
|---|---|---|---|---|---|---|---|---|
|  | PO puis, au cours de l' ECT: Midazolam 3 mg IV Alfentanyl 0,5 mg IV |  |  |  | puis 0 | +++ | edema; electrode (hyper pigmentation) epidermal erosion for 1 nodule |  |
| ROL | Lorazepan 2,5 Po Midazolam 3 mg IV Fentanyl 50 µg IV | 1$^{(1)}$ | 15 | 4 | + | ++ | Slight local edema | NC of size, disappearance of local pain |
| ALM | Lorazepam 2,5 mg PO Hydroxyzine 100 mg PO Morphine. HCl 10 mg SC puis Midazolam 5,5 mg IV Alfentanyl 1,5 mg IV | 6 | 15 | 4 | ++ | ++ | None | Growth retarded with respect to the very rapid increase in size of the untreated nodules |
| BRU | Levomepromazine 25 mg IM | 1$^{(2)}$ | 15 | 4 | 0 | + | Slight local edema | 1 RPL/15 Days |
| FAG | Levomepromazine 25 mg IM | 1$^{(3)}$ | 17 | 4 | 0 | + | None | NC |
| MIC 1 | Levomepromazine 25 mg IM puis Midazolam 3,5 mg IV Alfentanyl 0,25 mg IV | 3 | 15 | 8 | +++ | + | Local edema; leukonecrosis; late epidermal erosion; scabs | 3 RPL/36 Days |
| MIC 2 | Levomepromazine 25 mg IM Midazolam 3 mg IV Fentanyl 50 µg IV puis Midazolam 5 mg IV | 8$^{(4)}$ | 17 | 8 | + | +/++ | Local edema; leukonecrosis; late epidermal erosion; scabs | 5 RPL/12 Days |
| ROM | Levomepromazine 25 mg IM | 2$^{(5)}$ | 15 | 8 | + | + | Electrode marks | 2 RCL/22 Days |

Table 6: Individual electrochemotherapy conditions and effects. FAR and MIC were treated twice, respectively with intervals of 2 or 3 weeks. PO: per os; IM: intramuscular; IV: intravenous; SC: subcutaneous; Mod: number of treated nodules [($^1$): large nodule; ($^2$): idem treated with 3 runs of electric pulses; ($^3$): large transcutaneous permeation treated with 17 runs; ($^4$): 1 of them treated with 2 and 4 runs; ($^5$): treated with 2 and 3 runs]; BLM: amount of bleomycin; n: number of pulses comprised in each run; PL: pain level (0=absence; += unpleasant sensation; ++=bearable pain; +++=patient requiring increased analgesia or stopping the ECT); Contr: contractions (+=restricted to muscles localized beneath the nodules; ++=extended to muscles of the neck and shoulders homolaterally; +++=also extended contralaterally); LCR: local complete response, i.e., absence of any clinical trace of the nodule; LPR: local partial response.

Although the invention has been described with reference to specific examples, it should be understood that various modifications can be made without departing from the spirit of the invention. Accordingly, the invention is limited only to the following claims:

I claim:

1. A method of treating a human patient having at least one tumor cell comprising:

administering a chemotherapeutic composition to the human patient by systemic, local or direct tumor injection such that the composition is delivered to the cell;

applying an electrical impulse(s) via electroporation to the human patient transcutaneously and at the site of the tumor cell(s), of a sufficient strength and time for the impulse to cause electroporation of the tumor cell whereby the chemotherapeutic composition is delivered across the cell membrane, and wherein the delivery due to electroporation provides reduced toxicity and reduced side effects as compared with administering the chemotherapeutic composition in the absence of electroporation.

2. The method according to claim 1, wherein the composition is a non permeant molecule.

3. The method according to claim 1, wherein the composition is a anticancer drug.

4. The method according to claim 3, wherein the anticancer drug is bleomycin.

5. The method according to claim 1, wherein the composition is a cytotoxic drug.

6. The method according to claim 1, wherein the electrical impulse(s) is comprised of square wave pulses, exponential waves, unipolar oscillating wave forms of limited duration, bipolar oscillating wave forms of limited duration, or other wave forms generating electric fields.

7. The method according to claim 1, wherein the electrical impulse(s) is comprised of square wave pulses.

8. The method according to claim 1, wherein the electrical impulse applied is approximately 1.2 to approximately 1.5 kV/cm.

9. The method of claim 1 wherein the frequency of the impulse applied is approximately 1 Hertz.

* * * * *